(12) United States Patent
Dong et al.

(10) Patent No.: US 7,829,575 B2
(45) Date of Patent: Nov. 9, 2010

(54) METHODS FOR TREATING ANDROGEN RECEPTOR RELATED DISORDERS

(75) Inventors: Zhongyun Dong, Cincinnati, OH (US); Shan Lu, Cincinnati, OH (US)

(73) Assignee: University of Cincinnati, Cincinnati, OH (US)

( * ) Notice: Subject to any disclaimer, the term of this patent is extended or adjusted under 35 U.S.C. 154(b) by 868 days.

(21) Appl. No.: 11/787,593

(22) Filed: Apr. 17, 2007

(65) Prior Publication Data

US 2008/0015207 A1  Jan. 17, 2008

Related U.S. Application Data

(60) Provisional application No. 60/792,566, filed on Apr. 17, 2006.

(51) Int. Cl.
    *A61K 31/513* (2006.01)
(52) U.S. Cl. .................................. 514/274
(58) Field of Classification Search ............ 514/274
    See application file for complete search history.

(56) References Cited

OTHER PUBLICATIONS

Carter et al. Chemotherapy of cancer, Second edition, 1981, A wiley Medical Publication John Wiley & Sons, pp. 361-369.*
Yan et al, Heparin-binding keratinocyte growth factor is a candidate stromal to epithelial cell andromedin, Molecular Endocrinology (1992), 2123-2128, 6:12.
Cohen et al, Biological effects of prostate specific antigen as an insulin-like growth factor binding protein-3 protease, Journal of Endocrinology (1994), 407-415.
Fong et al, Regulation of prostatic carcinoma cell proliferation and secretory activity by extracellular matrix and stromal secretions, Prostate (1992), 21:121-131.
Yoshida et al, Prostate-specific antigen activates single-chain urokinase-type plasminogen activator, Int. J. Cancer (1995), 63:863-865.
Riegman et al, The promoter of the prostate-specific antigen gene contains a functional androgen responsive element, Molecular Endocrinology (1991), 1921-1930.
Kelly et al, Prostate specific antigen decline after antiandrogen withdrawal: the flutamide withdrawal syndrome, Int. J. of Urology (1992), 607-609.
Crawford et al, Challenges in the management of prostate cancer, Br. J. Urol. (1992), 70 Suppl. 1:33-38.
Jemal A. Murray T., Ward E., et al, Cancer statistics, 2005. CA Cancer J. Clin 2005; 55(1):10-30.
Culig Z., Role of the androgen receptor axis in prostate cancer. Urology 2003; 62(5 Suppl 1):21-6.
Grossman M.E., Huang H., Tindall D.J., Androgen receptor signaling in androgen-refractory prostate cancer. J. Natl Cancer Inst. 2001; 93(22):1687-97.

Scher H.I. Sawyers C.L., Biology of progressive, castration-resistant prostate cancer: directed therapies targeting the androgen-receptor signaling axis. J. Clin Oncol 2005; 23(32):8253-61.
Best C.J., Gillespie J.W., Yi Y., et al., Molecular alterations in primary prostate cancer after androgen ablation therapy. Clin Cancer Res 2005; 11(19 Pt 1):6823-34.
Eder I.E., Haag P., Basik M., et al., Gene expression changes following androgen receptor elimination in LNCaP prostate cancer cells. Mol Carcinog 2003;37(4):181-91.
Gregory C.W., Johnson R.T., Jr., Presnell S.C., Mohler J.L., French F.S., Androgen receptor regulation of G1 cyclin and cyclin-dependent kinase function in the CWR22 human prostate cancer xenograft. J. Androl 2001;22(4):537-48.
Lu S. Tsai SY, Tsai MJ. Regulation of androgen-dependent prostatic cancer cell growth: androgen regulation of CDK2, CDK4, and CKI p16 genes. Cancer Res 1997;57(20):4511-6.
Zhang M., Latham D.E., Delaney M.A., Chakravarti A., Survivin mediates resistance to antiandrogen therapy in prostate cancer. Oncogene 2005;24(1 5):2474-82.
Mabjeesh N.J., Willard M.T., Frederickson C.E., Zhong H., Simons J.W., Androgens stimulate hypoxia-inducible factor 1 activation via autocrine loop of tyrosine kinase receptor/phosphatidylinositol 3'-kinase/protein kinase B in prostate cancer cells. Clin Cancer Res 2003:9(7):2416-25.
Pandini G., Mineo R., Frasca F., et al., Androgens up-regulate the insulin-like growth factor-I receptor in prostate cancer cells. Cancer Res 2005;65(5):1849-57.
Chen C.D., Welsbie D.S., Tran C., et al., Molecular determinants of resistance to antiandrogen therapy. Nat Med 2004;10(1):33-9.
Balk S.P., Ko Y.J., Bubley G.J., Biology of prostate-specific antigen. J Clin Oncol 2003;21(2):383-91.
Diamandis E.P., Yousef G.M., Human tissue kallikreins: a family of new cancer biomarkers. Clin Chem 2002;48(8): 1198-205.
Webber M.M., Waghray A., Bello D.., Prostate-specific antigen, a serine protease, facilitates human prostate cancer cell invasion. Clin Cancer Res 1995;1(10):1089-94.

(Continued)

*Primary Examiner*—Jennifer M Kim
(74) *Attorney, Agent, or Firm*—Dinsmore & Shohl LLP

(57) ABSTRACT

One embodiment is directed toward a method for treating an individual with a disorder affected by androgen receptor activity. This method includes administering a therapeutic amount of DL3 (6-amino-2-(2-4-tert-butyl-phenoxy)-ethylsulfanyl)-1H-pyrimidin-4-one) to the individual. In an additional embodiment, the disorder affected by androgen receptor activity includes cancer. Another embodiment is directed toward a method for treating an individual with prostate cancer. This method includes administering to the individual a therapeutic amount of an androgen receptor antagonist which reduces the production of prostate specific antigen and has only negligible androgen receptor agonist effects.

16 Claims, 12 Drawing Sheets

OTHER PUBLICATIONS

Cramer S.D., Chen Z., Peehl D.M., Prostate specific antigen deaves parathyroid hormone-related protein in the PTH-like domain: inactivation of PTHrP-stimulated cAMP accumulation in mouse osteoblasts. J. Urol 1996;156(2 Pt 1):526-31.

Nadiminty N., Lou W, Lee S.O., et al., Prostate-Specific Antigen Modulates Genes Involved in Bone Remodeling and Induces Osteoblast Differentiation of Human Osteosarcoma Cell Line SaOS-2. Clin Cancer Res 2006;12(5):1420-30.

Kim J., Coetzee G.A., Prostate specific antigen gene regulation by androgen receptor. J Cell Biochem 2004;93 (2):233-41.

Cleutjens K.B., van der Korput H.A., van Eekelen C.C., van Rooij H.C., Faber P.W., Trapman J., An androgen response element in a far upstream enhancer region is essential for high, androgen-regulated activity of the prostate-specific antigen promoter. Mol Endocrinol 1997;1 1(2):148-61.

Schuur E.R., Henderson GA, Kmetec L.A., Miller J.D., Lamparski HG., Henderson D.R., Prostate-specific antigen expression is regulated by an upstream enhancer. J Biol Chem 1996;271(12):7043-51.

Miyamoto H., Rahman M.M., Chang C., Molecular basis for the antiandrogen withdrawal syndrome. J Cell Biochem 2004;91(1):3-12.

Middleman MN., Lush R.M., Sartor O., Reed E., Figg W.D., Treatment approaches for metastatic cancer of the prostate based on recent molecular evidence. Cancer Treat Rev 1996;22(2):105-18.

Hara T., Miyazaki J., Araki H., et al., Novel mutations of androgen receptor a possible mechanism of bicalcutamide withdrawal syndrome. Cancer Res 2003;63(1):149-53.

Yoshida T., Kinoshita H., Segawa T., et al., Antiandrogen bicalutamide promotes tumor growth in a novel androgen-dependent prostate cancer xenograft model derived from a bicalutamide-treated patient. Cancer Res 2005;65(21): 9611-6.

Huan S.D., Gerridzen R.G., Yau J.C., Steward D.J., Antiandrogen withdrawal syndrome with nilutamide. Urology 1997;49(4):632-4.

Small E.J., Carroll P.R., Prostate-specific antigen decline after casodex withdrawal: evidence for an antiandrogen withdrawal syndrome. Urology 1994;43(3):408-10.

Akakura K., Akimoto S., Ohki T., Shimazaki J., Antiandrogen withdrawal syndrome in prostate cancer after treatment with steroidal antlandrogen chlormadinone acetate. Urology 1995;45(4):700-4; discussion 4-5.

Sella A., Flex D., Sulkes A., Baniel J., Antiandrogen withdrawal syndrome with cyproterone acetate. Urology 1998;52 (6):1091-3.

Horoszewicz J.S., Leong S.S., Kawinski E., et al. LNCaP model of human prostatic carcinoma. Cancer Res 1983;43 (4):1809-18.

Lu S., Tsai S.Y., Tsai M.J., Molecular mechanisms of androgen-independent growth of human prostate cancer LNCaP-AI cells. Endocrinology 1999; 140(11):5054-9.

Jain A., Lam A., Vivanco I., Carey M.F., Reiter R.E., Identification of an androgen-dependent enhancer with the prostate stem cell antigen gene. Mol Encocrinol 2002; 16(10):2323-37.

Watt F., Martorana A., Brookes D.E., et al., A tissue-specific enhancer of the prostate-specific membrane antigen gene, FOLH1. Genomics 2001;73(3):243-54.

Murphy C., McGurk M.., Pettigrew J., et al., Nonapical and cytoplasmic expression of interleukin-8, CSCR1, and CXCR2 correlates with cell proliferation and microvessel density in prostate cancer. Clin Cancer Res 2005; 11(11): 4117-27.

Uehara H., Troncosco P., Johnston D., et al., Expression of interleukin-8 gene in radical prostatectomy specimen is associated with advance alpha pathologic state. Prostate 2005;64(1):40-9.

Lee C., Sutkowski D.M., Sensibar J.A., et al. Regulation of proliferation and production of prostate-specific antigen in androgen-sensitive prostatic cancer cells, LNCaP, by dihydrotestosterone. Endocrinology 1995;136(2)796-803.

Mohler J.L., Gregory C.W., Ford O.H., 3rd et al., The androgen axis in recurrent prostate cancer. Clin Cancer Res 2004;10(2):440-8.

Sramkoski, R.M., Pretlow, T.G., 2nd, Giaconia, J.M., et al., A new human prostate carcinoma cell line, 22Rv1, In Vitro Cell Dev. Biol. Anim., 1999; 35:403-9.

Lu, S., Dong, Z., Characterization of TGF-beta-regulated interleukin-8 expression in human prostate cancer cells, Prostate 2006; 66:996-1004.

Reid, J., Murray, I., Watts, K., Betney, R., McEwan, I.J., The androgen receptor interacts with multiple regions of the large subunit of general transcription factor TFIIF, J. Biol. Chem. 2002; 277:41247-53.

Zhang, J., Thomas, T.Z., Kasper, S., Matusik, R.J., A small composite probasin promoter confers high levels of prostate-specific gene expression through regulation by androgens and gluccocorticoids in vitro and in vivo, Endocrinology, 2000; 141:4698-710.

Gao, S., Liu, G.Z., Wang, Z., Modulation of androgen receptor-dependent transcription by resveratrol and genistein in prostate cancer cells, Prostate, 2004; 59:214-25.

Maggiolini, M., Vivacqua, A., Carpino, A., et al, The mutant androgen receptor T877A mediates the proliferate but not the cytotoxic dose-dependent effects of genistein and quercetin on human LNCaP prostate cancer cells, Mol. Endocrinol, 1999; 13:440-54.

\* cited by examiner

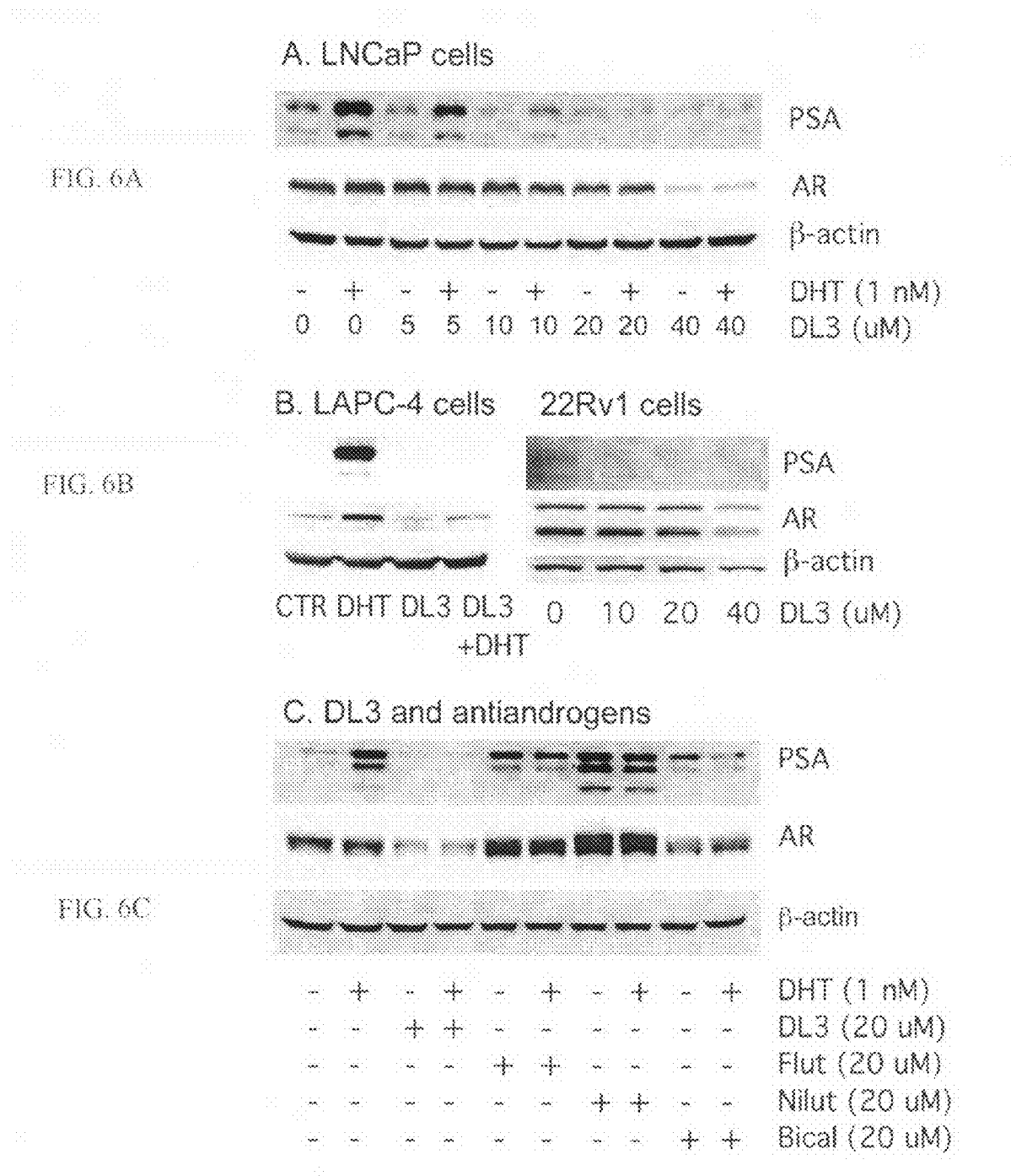

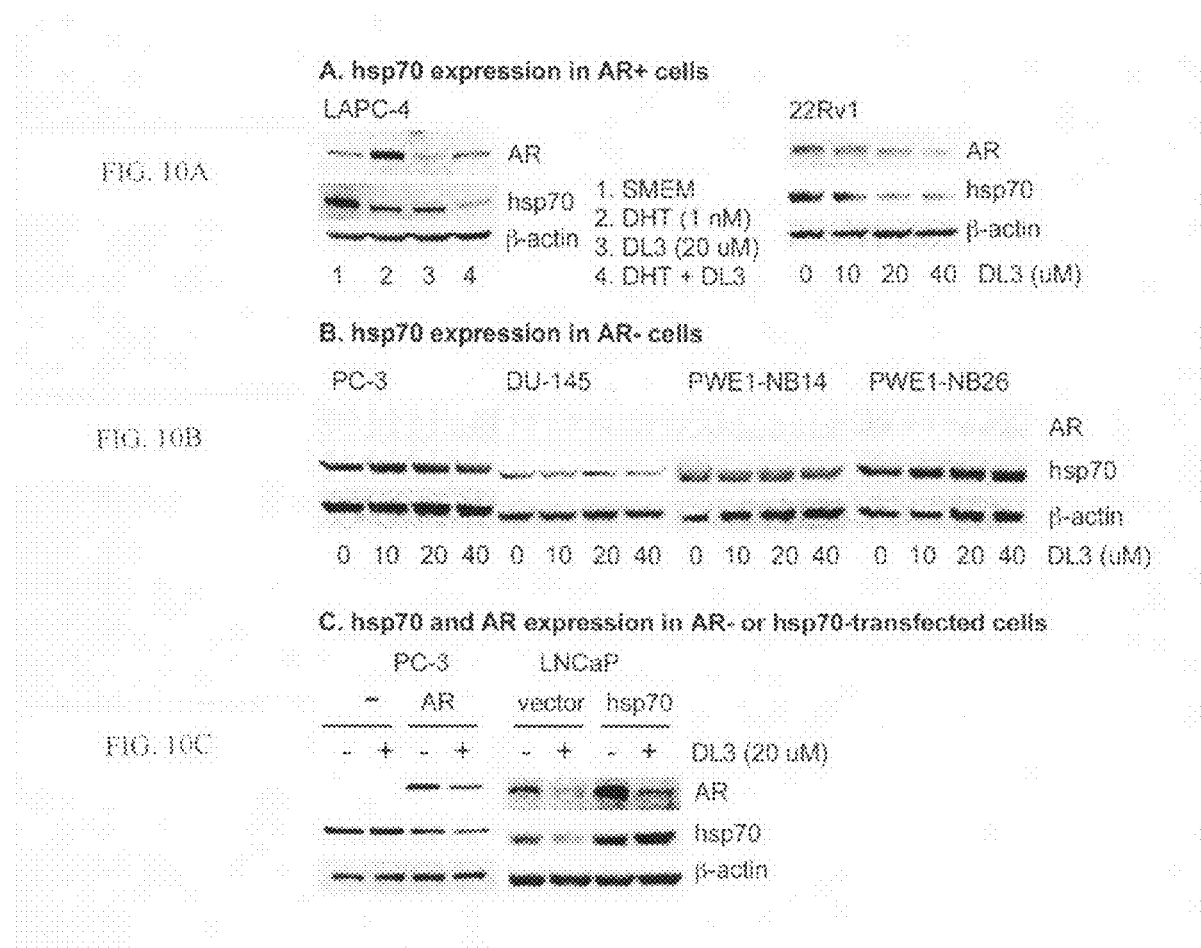

METHODS FOR TREATING ANDROGEN RECEPTOR RELATED DISORDERS

CROSS-REFERENCES TO RELATED APPLICATIONS

This application claims the benefit of U.S. Provisional Application No. 60/792,566, filed Apr. 17, 2006.

FIELD OF THE INVENTION

The present invention is directed to methods for treating androgen receptor related disorders.

BACKGROUND OF THE INVENTION

The androgen receptor (AR), a member of the steroid receptor superfamily, is a ligand-dependent transcription factor that mediates androgen action in cells and has been linked to many disorders like, balding, benign prostatic hyperplasia and prostate cancer. The AR is composed of three major domains: an $NH_2$-terminal transcriptional activation domain, a central DNA-binding domain, and a COOH-terminal ligand-binding domain (LBD). The AR is associated with cellular chaperones in its inactive state, however, after binding to androgens such as testosterone and dihydrotestosterone (DHT), the AR undergoes a conformation change and dissociates from its cellular chaperones. The AR forms homodimers and interacts with coactivators and chromatin modifying enzymes, and it also binds to androgen-response elements (ARE) within the genome. These ARE regulate expression of genes relevant to prostatic growth and function. Additionally, ARE have been linked to cancer development and progression. Among the numerous genes regulated by the AR, AR activation has been shown to upregulate expression of prostate specific antigen (PSA), cyclin-dependent kinases (cdk) 1, 2 and 4, cyclin A and B, keratinocytes growth factor, survivin, hypoxia-inducible factor-1a, and insulin-like growth factor-1 receptor (IGF-IR). Moreover, AR mutation, amplification, and/or overexpression often occur and are involved in the development of androgen-independent growth of prostate cancer.

Prostate cancer is the most common cancer and the second most common cause of cancer death among men in the United States. It is expected that 218,890 men will be diagnosed with and 27,050 men will die from this disease in 2007. As detection techniques improve, an increasing number of patients are diagnosed with localized disease, whereas the number of patients with disseminated diseases are on the decline. Metastasis, however, still occurs prior to the initial diagnosis in many patients, and hence eradication of primary tumors by either surgery or radiation therapy is not curative. Because prostate cancer is insensitive to most chemotherapeutic agents clinically available, hormonal manipulations are the mainstay treatment for advanced disease. Current hormonal therapies, however, are palliative and can only slow the progression of advanced prostate cancer by an average of less than 18 months. As such, there is an urgent need to develop more effective therapeutic modalities for both prostate cancer and for other disorders affected by androgen receptor activity.

SUMMARY OF THE INVENTION

One embodiment of the present invention is directed toward a method for treating an individual having a disorder affected by androgen receptor activity. This method includes administering a therapeutic amount of DL3 (6-amino-2-(2-4-tert-butyl-phenoxy)-ethylsulfanyl)-1H-pyrimidin-4-one) to the individual.

Another embodiment of the present invention is directed toward a method for treating an individual having prostate cancer. This method includes administering to the individual a therapeutic amount of an androgen receptor antagonist which reduces the production of prostate specific antigen and has no measurable androgen receptor agonist effects.

Another embodiment of the present invention is directed toward a method for treating an individual having cancer affected by androgen receptor activity. The method includes administering a therapeutic amount of DL3 (6-amino-2-(2-4-tert-butyl-phenoxy)-ethylsulfanyl)-1H-pyrimidin-4-one) to the individual.

Additional embodiments, objects and advantages of the invention will become more fully apparent in the detailed description below.

BRIEF DESCRIPTION OF THE DRAWINGS

The following detailed description will be more fully understood in view of the drawings in which:

FIGS. 6A-6C are western blots showing the effects of DL3 on cellular PSA and AR protein expression according to one embodiment;

FIGS. 10A-10C is a set of illustrations showing AR-dependent down regulation of hsp70 by DL3 according to one embodiment;

Figure 1:
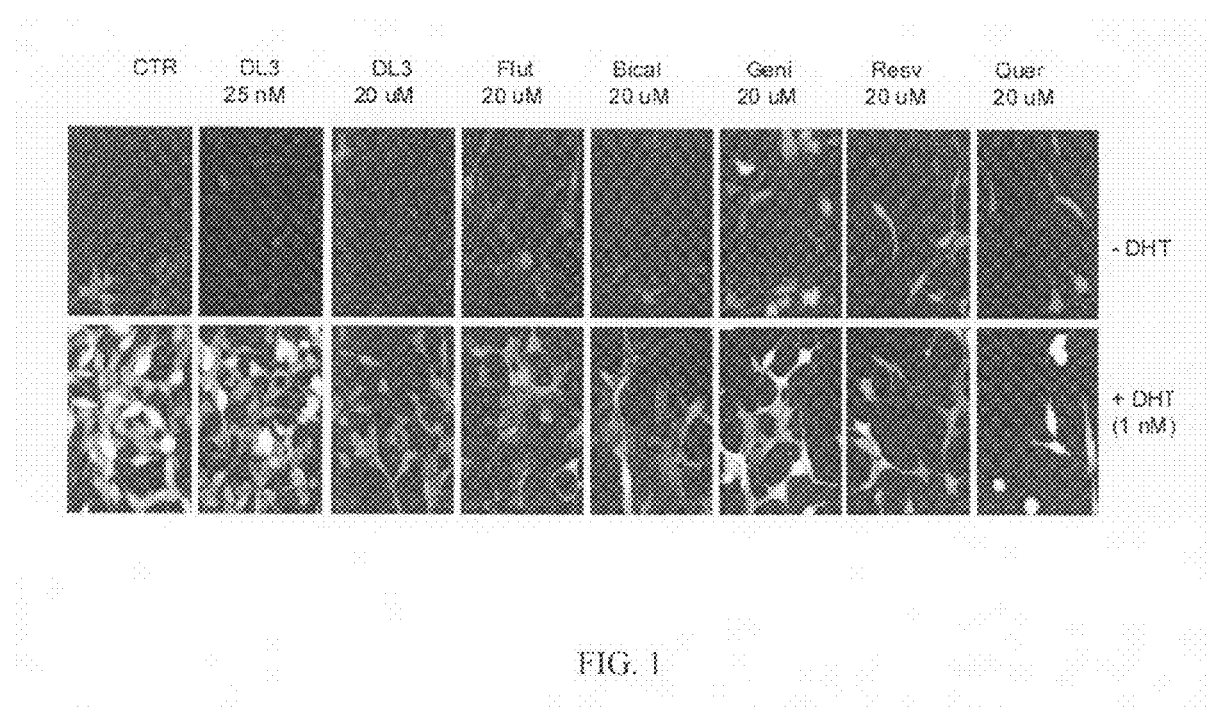
FIG. 1 is a set of pictures showing the effects of DL3 and several other compounds on GFP expression according to one embodiment.

The embodiments set forth in the drawings are illustrative in nature and are not intended to be limiting of the embodiments as defined by the claims. Moreover, individual features of the drawings and the embodiments will be more fully apparent and understood in view of the detailed description.

DETAILED DESCRIPTION

Many disorders are linked to androgen and to androgen receptors. These diseases include balding, benign prostatic hyperplasia, prostate cancer, etc. Many of these diseases are treated with hormone therapy, but this treatment can be ineffective or can become ineffective over time. However, by directing treatment toward the androgen receptor, many additional beneficial effects are recognized, including, preventing potentially harmful genes down stream of the AR from being activated.

The compound 6-amino-2-(2-4-tert-butyl-phenoxy)-ethylsulfanyl-1H-pyrimidin-4-one (DL3 for simplicity) has been identified as treating disorders affected by androgen receptor activity and therefore as useful for affects androgen receptor activity.

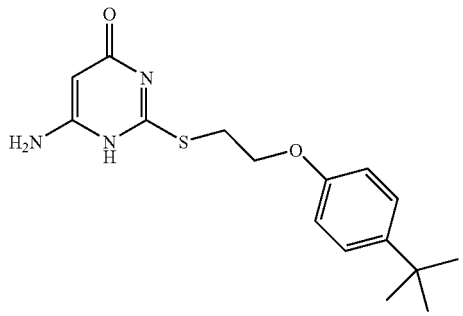

6-Amino-2-{2-(4-tert-βutyl-phenoxy)-ethylsulfanyl}-1H-pyrimidin-4-one

Therefore, one embodiment of the present invention is directed toward a method for treating an individual having a disorder affected by androgen receptor activity. This method includes administering a therapeutic amount of DL3 (6-amino-2-(2-4-tert-butyl-phenoxy)-ethylsulfanyl)-1H-pyrimidin-4-one) to the individual. It should be noted that treatment with DL3 as recited herein is contemplated to include salts of DL3 and other derivatives of DL3 which affect androgen receptor activity. In a further embodiment, the therapeutic amount of DL3 is administered at a concentration from about 1 µM to about 50 µM. In another embodiment, it is administered at a concentration from about 1 µM to about 10 µM. In a further embodiment, the disorder affected by androgen receptor activity is cancer. In another embodiment, the disorder includes at least one of balding, benign prostatic hyperplasia, and prostate cancer.

Among the numerous genes regulated by the AR, AR activation has been shown to upregulate the expression of prostate specific antigen (PSA). PSA, a 33 kD serine protease, is encoded by kallikrein (KLK)3, a member of 15 kallikrein gene family. In the normal prostate, PSA is produced primarily by ductal and acinar epithelium and is secreted into the glandular ducts to degrade high molecule weight protein and to prevent coagulation of the semen. Because of the loss of the normal glandular architecture in tumor tissues, high levels of PSA leak into serum. This is a widely used serologic marker to determine prostate cancer burden in cancer diagnosis, prognosis, and therapy response. In addition, it has been reported that PSA may promote prostate cancer progression by releasing IGF-1, a growth factor for prostate cancer cells, and by cleaving extracelluar matrix, urokinase-type plasminogen activator, and parathyroid hormone-related protein. Additionally, it is believed that PSA may even be involved in bone metastasis.

PSA is produced by both AR-dependent and -independent prostate cancer cells. Expression of PSA as well as KLK2 is primarily regulated at transcriptional level by AR signaling axis. There is an ARE (−156 to −170 base pairs) and a weak nonconsensus ARE (−365 to −400 base pairs), termed androgen response region (ARR), in the PSA proximal promoter region. In addition, a PSA distal enhancer consisting of an additional ARE (ARE III) and several weak AREs were mapped at approximately 4.2 kb upstream of the transcription start site.

Current treatments directed toward reducing PSA include nonsteroidal antiandrogens which are small molecule antagonists of AR. There are three nonsteroidal antiandrogens, Flutamide (Eulexin), Nilutamide (Nilandron), and Bicalutamide (Casodex), currently available in the US. They have been administered both as monotherapy and in combination with testicular androgen suppression (by either surgical or medical orchiectomy), for management of disseminated prostate cancer. Antiandrogens competitively inhibit the binding of androgens to the LBD of the AR, block AR activation, suppress tumor growth, and reduce serum PSA. Although most tumors regress initially in response to these therapies, they recur during the therapies in an androgen-independent manner in less than 18 months. Numerous studies show that high levels of the AR and AR-regulated genes are expressed in recurrent prostate cancer. Furthermore, it has been shown that androgens in recurrent prostate cancer tissues are sufficient to activate the AR. In some patients, these antiandrogens can even promote the growth of androgen-refractory tumors, causing androgen withdrawal syndrome. If this syndrome arises, discontinuation of the antiandrogen treatment results in clinical improvement and a fall in serum PSA. This antiandrogen withdrawal (AAW) syndrome is also observed in patients receiving steroidal antiandrogens. The AAW syndrome is caused possibly by weak AR agonistic effects of the antiandrogens.

The failure in hormonal therapy, resulting from the development of androgen-independent growth, is an obstacle for successful management of advanced prostate cancer. Compelling data demonstrates that AR is expressed in most prostate cancer cells and overexpression of AR is necessary and sufficient for androgen-independent growth of prostate cancer cells. Therefore, downregulation of AR is the most promising direction in developing drugs for therapy against advanced prostate cancer. DL3 has been identified as downregulating AR expression and inhibiting DHT-induced cell growth and gene expression. In comparison with the three classical antiandrogens, DL3 is much more potent and has no detectable intrinsic AR agonist activity on AR-regulated gene expression and cell growth in the absence of androgen. Moreover, it inhibits DHT-induced gene expression and cell growth in cells resistant to the antiandrogens Flutamide (Flut) or Nilutamide (Nilut). Protein docking analysis implies that DL3 can bind to the LBD of AR. These data show that DL3 is a novel antiandrogen and is suitable for therapy against advanced prostate cancer.

Figure 2:
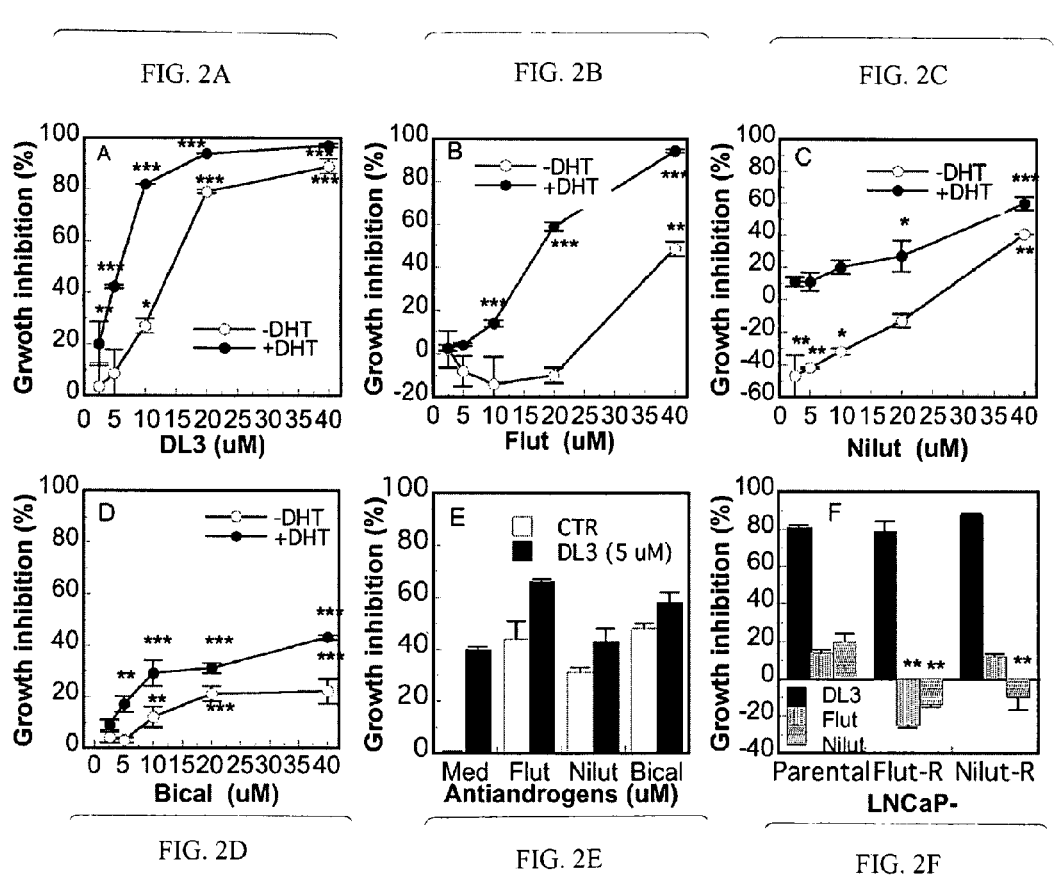
FIGS. 2A-2F show the inhibitory effects of DL3 on cell growth according to one embodiment.
Figure 3:
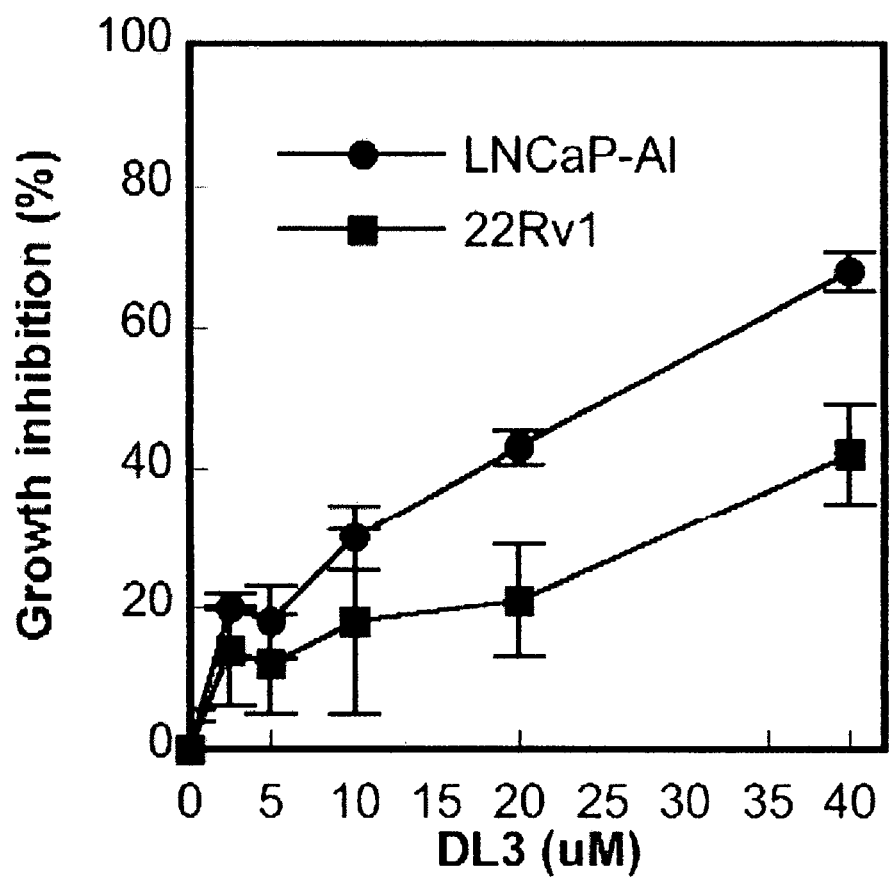
FIG. 3 shows the effects of DL3 on the growth of other cell lines according to one embodiment.

Therefore, another embodiment is directed toward a method for treating prostate cancer including administering to an individual having prostate cancer a therapeutic amount of an androgen receptor antagonist which reduces the production of PSA and has no measurable androgen receptor agonist effects. Discerning whether the androgen receptor antagonist has no measurable AR agonist effects is illustrated in FIGS. 1-3 and their corresponding discussion. For example, the failure to induce AR-regulated GFP expression indicates only negligible or no measurable AR agonist effects.

In one embodiment, the therapeutic amount is administered at a concentration from about 1 µM to about 50 µM. In another embodiment, the concentration is from about 5 µM to about 20 µM. The concentration of the therapeutic amount can also depend on the presence or co-administration of an androgen. When administered with an androgen, a lesser concentration may be required (for example, from about 1 µM to about 10 µM), but when administered in the absence of an androgen, a higher concentration is required (for example, from about 5 μM to about 40 μM).

In addition to being a monotherapy, embodiments also include additional co-therapies. For example, for treating benign prostatic hyperplasia, the androgen receptor antagonist can be administered in addition to finasteride. For cancer treatment, for example, the androgen receptor antagonist can be administered in addition to chemotherapy or a nonsteroidal antiandrogen.

The androgen receptor antagonist may be administered by any suitable route or device. In once embodiment, the antagonist will be administered orally. The most common form of delivery will be a tablet. In other embodiments, the form of delivery will be a capsule, caplet and/or quick dissolve strip. In another embodiment, the antagonist will be administered transdermally. The most common form of transdermal delivery will be with an adhesive patch. In another embodiment, the antagonist can be delivered via an injection.

The androgen receptor antagonist is administered in an amount sufficient to treat the disorder affected by androgen receptor activity. In one embodiment, the therapeutic amount is from about 50 mg/day to about 500 mg/day. This is similar to the dosing requirements of bicalutamide for the management of human prostate cancer. The treatment as used herein encompasses a reduction in clinical symptoms of the disorder and/or elimination of the disorder. Therapeutic amounts will vary based on an individual's age, body weight, symptoms, and the like, and may be determined by one of skill in the art in view of the present disclosure.

Example

DL3 does not have AR agonist activity on AR-regulated GFP expression. In FIG. 1, LNCaP-ARR$_2$-GFP cells are cultured in SMEM in the absence or presence of 1 nM of DHT and the compounds as indicated. From FIG. 1, it is seen that DL3 does not induce GFP expression in LNCaP-ARR$_2$-GFP cells at the concentrations of either 25 nM or 20 μM. In contrast, although Genistein, Resveratol, and Querstin significantly inhibited cell growth, they all enhanced GFP expression in the absence of DHT (FIG. 1), suggesting the intrinsic AR agonist activity, which has been reported by others. This DHT-independent expression of GFP is also observed in LNCaP-ARR$_2$-GFP cells treated with Flut but not Bical (FIG. 1). DL3 inhibits cell growth and has no agonist activity on cell growth in the absence of DHT In FIG. 2 A-D, LNCaP cells are starved in SMEM for 3 days and then incubated for 4 days with fresh SMEM in the absence or presence of 1 nM of DHT. In FIG. 2E, LNCaP cells are incubated for 4 days in MEM supplemented with 10% FBS (complete MEM, CMEM) in the presence or absence of 5 μM DL3 and/or 10 μM of Flut, Nilut, or Bical. For FIG. 2F, LNCaP cells are cultured in CMEM in the presence of 10 μM of Flut or Nilut for over 2 months to derive LNCaP-Flut-R and LNCaP-Nilut-R cells. LNCaP, LNCaP-Flut-R, or LNCaP-Nilut cells are treated for 4 days with 10 μM of DL3, Flut, or Nilut. Viable cells are stained with MTT (3-(4,5-dimethylthiazol-2-yl)-2,5-diphenyltetrazolium bromide). *, , and * designate p<0.05, <0.01, and 0.001, respectively, compared with controls. Thus, looking at FIG. 2, DL3 inhibits DHT-stimulated growth of LNCaP cells (mutant AR, H877A) in a dose-dependent manner and its inhibition reaches a plateau at concentrations greater than 10 μM (FIG. 2A). Similar inhibitory effects on DHT-stimulated cell growth are observed in LAPC-4 (wildtype AR, data not shown) and 22Rv1 (mutant AR, H874Y) cells (FIG. 3). DL3 also inhibits growth of LNCaP cells in the absence of DHT, but requires higher concentrations. At 10 μM of DL3, the growth of LNCaP cells in the presence and absence of DHT is inhibited by 82% and 27%, respectively. Flut (FIG. 2B), Nilut (FIG. 2C), and Bical (FIG. 2D), also inhibit DHT-stimulated growth of LNCaP cells in a dose-dependent manner, but at potencies much inferior to that of DL3. On the other hand, although both Flut and Nilut inhibit cell growth under DHT-free conditions at 40 μM, they promote cell growth in the absence of DHT at concentrations up to 20 μM (FIGS. 2B and 2C). No significant additive effect is observed when LNCaP cells are treated with DL3 and Flut, Nilut, or Bical (FIG. 2E). Without being limited by theory, it is believed that DL3 and the three antiandrogens inhibit cell growth through similar mechanisms.

Next, the effects of DL3 are determined on the growth of LNCaP cells refractory to Flut or Nilut. The data in FIG. 2F shows that DL3 significantly inhibits growth of parental as well as the two lines of antiandrogen-refractory cells to similar extents. In contrast, Flut moderately inhibits growth of parental and LNCaP-Nilut-R cells, but promotes growth of LNCaP-Flut-R cells. Nilutamide moderately inhibits growth of parental cells, but promotes growth of the two lines of antiandrogen-resistant cells. Furthermore, growth of androgen-independent LNCaP-AI cells is also suppressed by DL3 in a dose-dependent manner. See, for example, FIG. 3 where LNCaP-A1 cells in SMEM and 22Rv1 cells in CMEM are cultured for four days with DL3, followed by MTT staining and 22Rv1 cells are obtained from ATCC.

Figure 4:
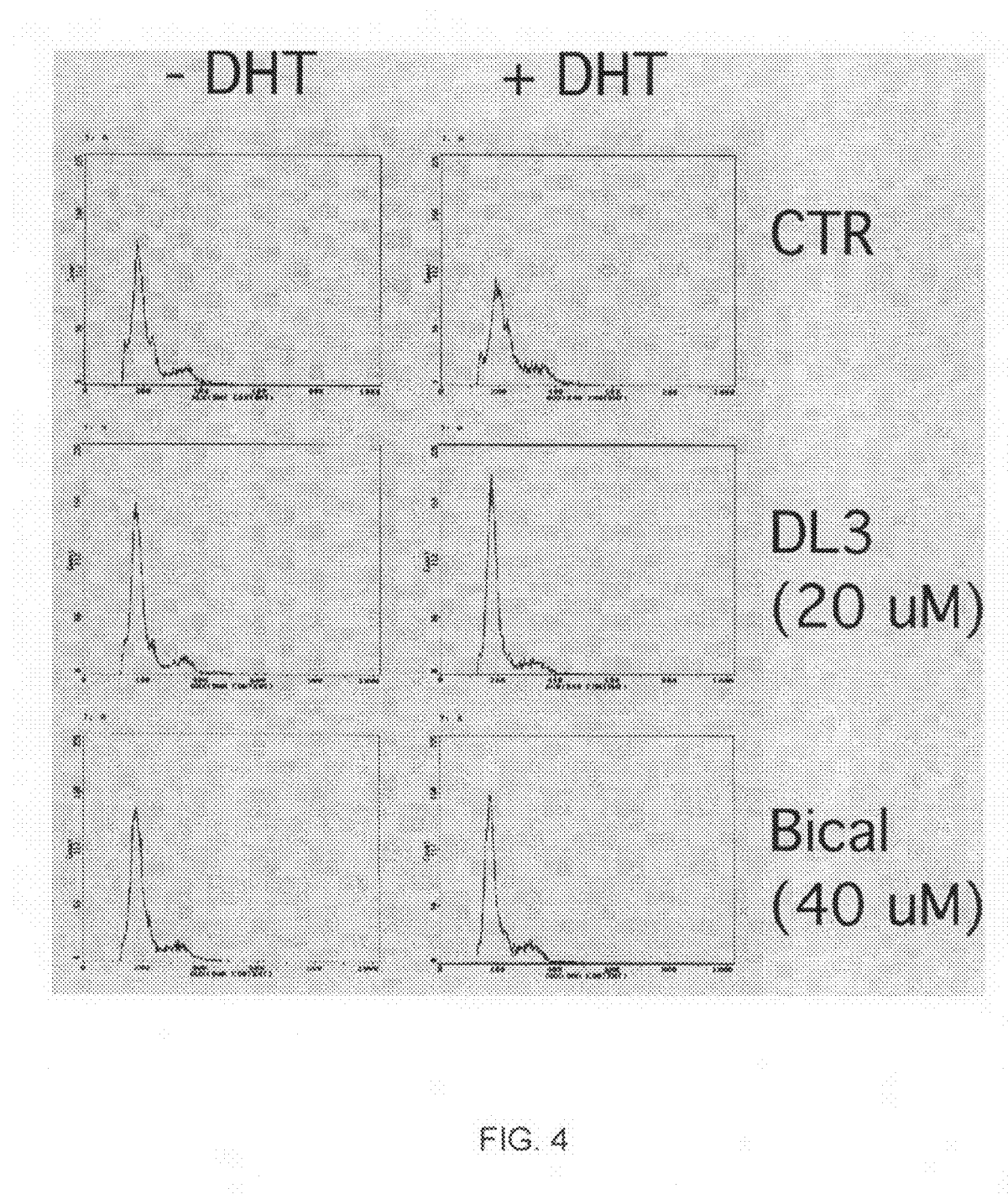
FIG. 4 shows the effects of DL3 and Bical on a cell cycle according to one embodiment.
Figure 5A:
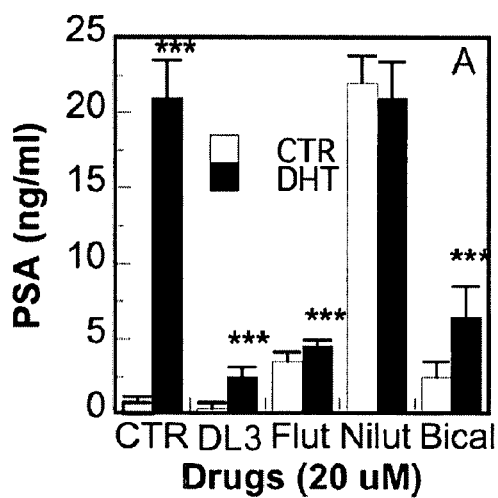
FIGS. 5A-5D show that DL3 inhibits PSA secretion according to one embodiment.
Figure 5B:
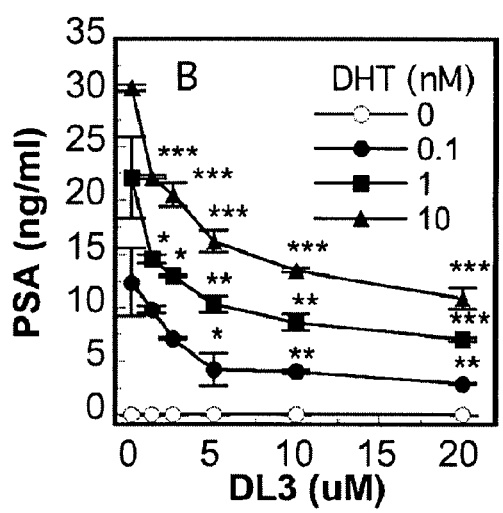
Figure 5C:
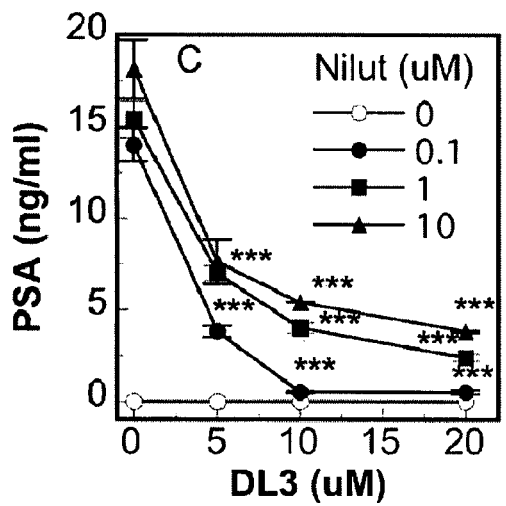
Figure 5D:
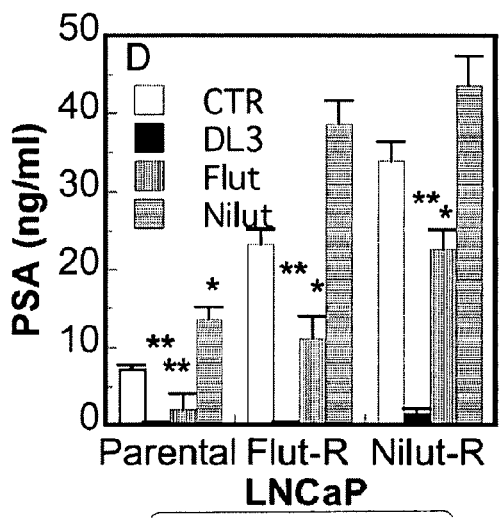
Figure 7A:
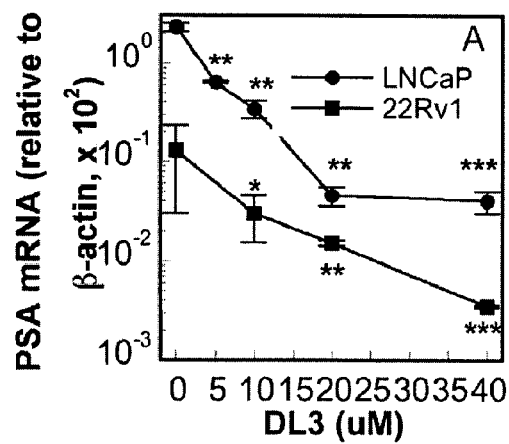
FIGS. 7A-7D show the effects of DL3 on PSA and AR mRNA expression according to one embodiment.
Figure 7B:
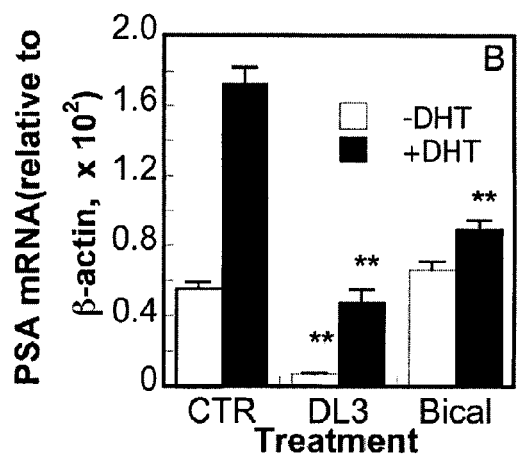
Figure 7C:
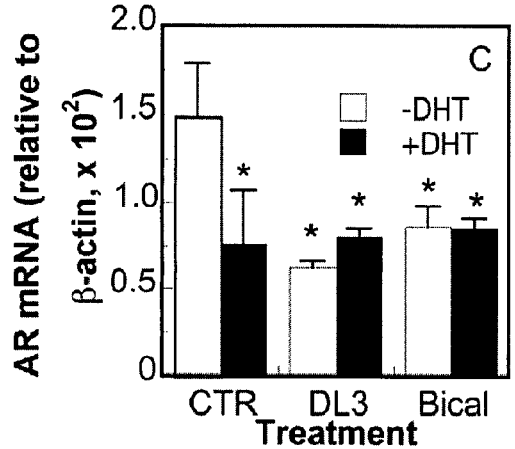
Figure 7D:
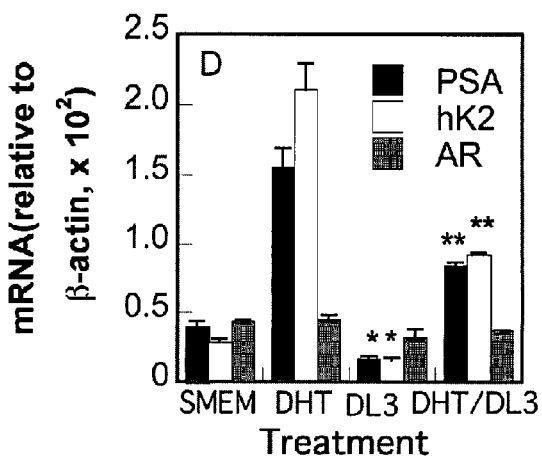

To further appreciate the effects of DL3 on cell growth, cell cycle distribution is determined using the flow cytometry analysis. After incubation of LNCaP cells for 24 hr in SMEM, the majority of cells are in the G1 phase of cell cycle. Many cells move to the S phase when cultured in the presence of 1 nM DHT. Treatment with DL3 or Bical (or Flut, not shown) significantly increase the portion of cells (by 15%) in G1 phase of cell cycle regardless of the presence or absence of DHT (FIG. 4). The treatment, however, does not induce apoptosis (FIG. 4). See, for example, FIG. 4 where LNCaP cells are starved in SMEM for 3 days and treated for 24 hr. with 1 nM DHT, DL3, and/or Bical. The cell cycle distribution is examined by the propidium staining method. The western blotting analysis reveals that treatment of LNCaP cells with DL3 as well as Bical alter neither survivin expression nor caspase 3 cleavage (data not shown), confirming that a treatment with DL3 at 20 μM for 24 hr does not induce apoptosis. Thus, DL3 induces GI arrest of prostate cancer cells in short term culture.

Inhibitory Effects of DL3 on Expression of AR and AR-Regulated Genes

For the following discussion, see FIG. 5, where androgen-starved LNCaP, LNCaP-Flut-R, or LNCaP-Nilut-R cells are plated into 96-well plates at 2×10$^4$ cells/wells in SMEM and treated for 48 hr. PSA in the culture supernatant is determined by using an enzyme-linked immunosorbent assay (ELISA) kit. PSA levels are normalized by cell density. For FIG. 6A, 1 nM DHT; 20 μM of DL3 and DHT are added. For FIG. 6C, various concentrations of DL3 and Nilut are added and for FIG. 6D, 1 nM DHT; 10 μM DL3, Flut, or Nilut. *,  , and * designate p<0.05, p<0.05, and p<0.001. Thus, LNCaP cells secrete very low basal levels of PSA in the absence of DHT, which is significantly elevated in cells incubated with 1 nM of DHT (FIG. 5A). Treatment with 20 μM of DL3 does not induce PSA production and inhibits the DHT-induced PSA production by approximately 90% (FIG. 5A). Unlike DL3, treatment with 20 μM of Flut or Bical, and much more potently with Nilut, stimulates PSA production under androgen-free conditions (FIG. 5A). Flut and Bical, but not Nilut, reduce DHT-induced PSA production (FIG. 5A). The inhibitory effects of DL3 on DHT-induced PSA production are dose-dependent and are partially reversed by increasing DHT concentrations, showing that the inhibition is due to a blockade of AR activity rather than nonspecific toxicity (FIG. 5B). The DHT-induced production of PSA is reduced by approximately 50% in cells treated with 5 µM of DL3 (FIG. 5B). Stimulatory effects of Nilut on PSA production in LNCaP cells are dose-dependent and are also blocked by DL3 (FIG. 5C). PSA production is elevated in LNCaP-Flut-R and LNCaP-Nilut-R cells compared with that in their parental cells (FIG. 5D). Inconsistent with its effects on cell growth (FIG. 3F), DL3 inhibits PSA production in all three lines of LNCaP cells to a similar extent. Although Flut also inhibits PSA production in both parental and drug-resistant cells, the extent of inhibition is reduced in cells refractory to Flut or Nilut (FIG. 5D). On the other hand, Nilut enhances PSA production on three lines of LNCaP cells (FIG. 5D).

As seen in FIG. 6, DL3 downregulates intracellular levels of PSA and AR. In FIG. 6, cellular PSA and AR are analyzed by western blotting androgen-starved LNCaP cells. In FIG. 6A cells in SMEM are treated for 24 hr with DL3 in the absence or presence of DHT. LAPC-4 (B, in SMEM) or 22Rv1 cells (B, in CMEM) are treated for 24 hr with 1 nM DHT, 20 µM DL3, or DHT plus DL3 (LAPC-4 cells) or with increasing concentrations of DL3 (22Rv1 cells). Androgen-starved LNCaP cells (C) in SMEM are treated for 24 hr with 20 µM of DL3, Flut, Nilut, or Bical.

LNCaP cells express a low basal level of PSA, which is significantly increased by DHT (FIG. 6A). The DHT-induced PSA expression is dose-dependently reduced by DL3 (FIG. 6A). The inhibitory effects of DL3 on DHT-induced PSA expression are also observed in LAPC-4 cells (wildtype AR) (FIG. 6B, left panel) and in 22Rv1 cells (FIG. 6B, right panel). Note that both LAPC-4 and 22Rv1 cells express much lower levels of PSA. The exposure of the membranes in FIG. 6B are 5-6 times longer than that in FIG. 6A. Treatment with Flut, Nilut, or Bical enhances PSA expression under androgen-free culture conditions (FIG. 6C). DHT-induced PSA expression is moderately reduced by Flut and Bical and is not altered by Nilut (FIG. 6C). The effects of DL3 on AR expression are also examined. As shown in FIGS. 6A and 6B, the expression of AR in both LNCaP and 22Rv1 cells is not significantly altered when treated with 5 and 10 µM of DL3, but is reduced in cells treated with 20 and 40 µM of DL3. AR expression is similarly reduced in LAPC-4 cells (FIG. 6B). Expression of AR is enhanced by Flut and Nilut, but is moderately downregulated by Bical (FIG. 6C).

DL3 downregulates PSA and AR mRNA expression as shown in FIG. 7. In FIG. 7 LNCaP or 22Rv1 cells (A) are treated for 24 hr with DL3 and total RNA is extracted and analyzed by real-time RT-PCR. Androgen-starved LNCaP cells are treated for 24 hr (B, C) or 6 hr (D) with 1 nM DHT and/or 20 µM DL3 or Bical and cellular RNA is analyzed by RT-PCR. Quantitative real-time RT-PCR analysis reveals that both LNCaP and 22Rv1 cells growing CMEM express PSA mRNA. PSA mRNA in LNCaP cells is approximately 20 fold higher than that in 22Rv1 cells (FIG. 7A). DL3 inhibits the expression of PSA mRNA in both LNCaP and 22Rv1 cells in a dose-dependent fashion (FIG. 7A). Treatment of LNCaP cells for 24 hr with 20 µM of DL3 significantly reduces the basal level of PSA mRNA and abolishes DHT-stimulated PSA mRNA expression (FIG. 7B). In contrast, treatment with 20 µM of Bical has no significant effects on the basal level of PSA mRNA and only partially inhibits DHT-stimulated PSA mRNA expression (FIG. 7B). Expression of AR mRNA is partially downregulated in cells treated for 24 hr with 1 nM of DHT, 20 µM of DL3 or Bical, or a combination of either DHT and DL3 or Bical (FIG. 7C). The similar inhibitory effects of DL3 on both basal and DHT-induced PSA, as well as hK2, expression is observed in cells treated for 6 hr with DL3 (FIG. 7D), indicating that the inhibition is an early event. In contrast, AR mRNA expression is not significantly altered in cells treated for 6 hr with either DHT or DL3 (FIG. 7D).

DL3 opposes effects of AR on expression of several other AR-regulated genes as shown in Table 1. To evaluate the specificity of the effects of DL3, expression of several other genes are determined by quantitative RT-PCR. The data in Table 1 shows that the treatment of LNCaP cells with DL3 significantly inhibits the expression of PSA (as a positive control), hK2, and prostate stem cell antigen (PSCA), which are all upregulated by AR signaling through ARE in their promoters. In contrast, DL3 enhances expression of prostate-specific membrane antigen (PSMA), which is repressed by AR activation. Enhancement of PSMA expression by DL3 is also observed at the protein level (Data not shown). On the other hand, expression of interleukin-8 (IL-8), also elevated in advanced prostate cancer cells but not regulated by AR, and is not significantly altered by DL3.

TABLE 1

Inhibition of the expression of AR-regulated genes by DL3

| Genes[1] | CTR | DL3[2] | DL3/CTR (%) |
|---|---|---|---|
| PSA | 9.51e−01 | 3.03e−02 | 3 |
| hK2 | 2.24e−02 | 4.05e−03 | 18 |
| PSCA | 3.45e−04 | 1.90e−04 | 55 |
| PSMA | 3.56e−02 | 1.35e−01 | 379 |
| IL-8 | 8.03e−04 | 8.59e−04 | 107 |

[1]Expression levels relative to β-actin.
[2]DL3 treatment: 20 µM for 24 hr.

DL3 inhibits PSA gene transcription and PSA promoter activity as shown in FIG. 8. In FIG. 8, androgen-starved LNCaP cells (A) are treated for 16 hr with 1 nM DHT and/or 20 µM DL3. Nuclei are isolated for real-time PCR-based nuclear run-on analysis. LNCaP cells (B) in SMEM are transfected for 24 hr with pGL3-PSA-luc and PC-3 cells (C) are co-transfected with pGL3-PSA-luc and pcDNA3-HA-AR, pcDNA3-AR-AF1 (LBD deleted), or pcDNA3-AR-AF2 (NTD deleted). The transfected cells are treated for 24 hr with 1 nM of DHT and/or 20 µM of DL3. Luciferase activity in the lysates is assessed by using a luciferase assay kit.

Figure 8A:
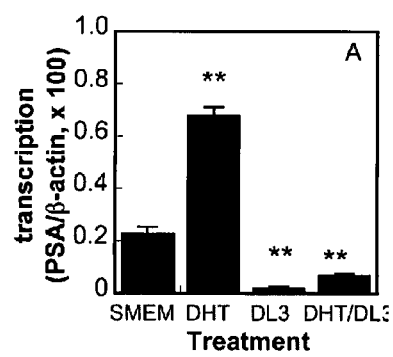
FIGS. 8A-8C show the effects of DL3 on PSA gene transcription and PSA promoter activity according to one embodiment.
Figure 8B:
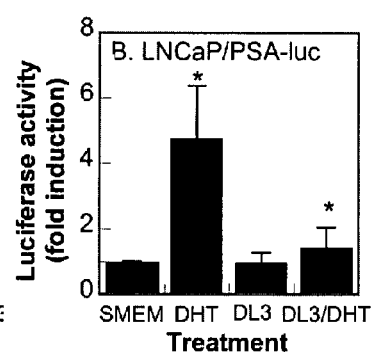
Figure 8C:
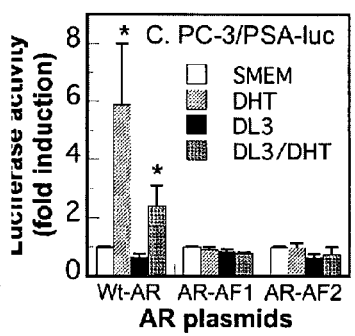

The nuclear run-on assay reveals that in vitro transcription of PSA mRNA by nuclear extracts isolated from DHT-treated cells is significantly elevated (FIG. 8A). In nuclear extracts isolated from cells treated with DL3, both the basal and DHT-induced PSA mRNA transcription activity is significantly reduced (FIG. 8B). LNCaP cells are transfected with a PSA reporter plasmid (pGL3-PSA-luc) in which the expression of luciferase is driven by 4.3 kb of human PSA gene promoter. The data in FIG. 8B shows that PSA promoter activity is enhanced by approximately 5 fold in DHT-treated cells. Treatment with 20 µM of DL3 alone does not significantly alter the basal PSA promoter activity and attenuates the activity induced by DHT (FIG. 8B). To examine the effects of DL3 on wildtype AR-induced PSA promoter activity, PC-3 cells are co-transfected with the PSA promoter luciferase reporter and a plasmid encoding wildtype AR, the constitutive active AR-AF1, or the weakly active AR-AF2. As shown in FIG. 8C, DL3 significantly inhibits DHT-induced activation of PSA promoter activity in cells transfected with wild-type AR. The magnitude of inhibition, however, is modest relative to reduction in PSA expression. DL3 does not inhibit activation of PSA promoter activity by AR-AF1 or AR-AF2 activity (FIG. 8C), indicating that DL3 specifically inhibits wildtype AR-regulated promoter activity.

Figures 9A, 9B, 9C:
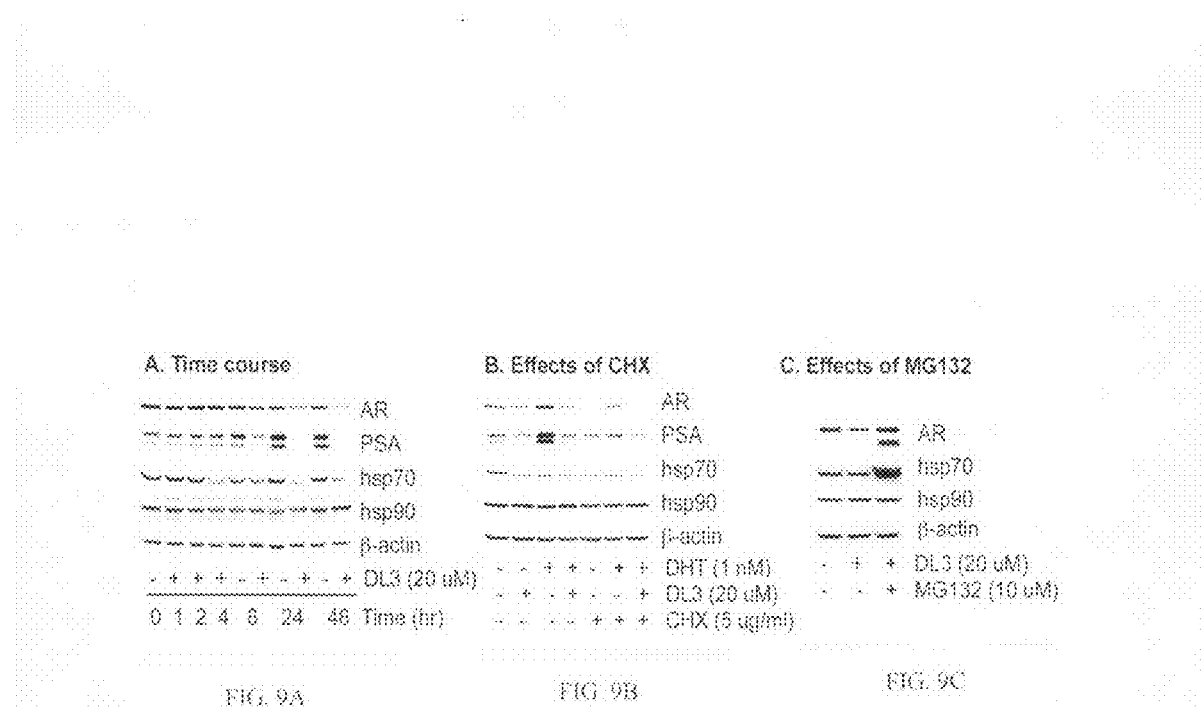
FIGS. 9A-9C is a set of illustrations showing the effects of DL3 on AR stability according to one embodiment.

DL3 reduces AR protein stability. Data in FIG. 9A clearly shows that DL3 downregulates AR protein levels in LNCaP cells (mutant AR, androgen sensitive) in a dose-dependent manner. In FIG. 9, LNCaP cells are incubated for various times with 20 µM DL3, androgen-starved LNCaP cells (B) are incubated for 24 hr with DHT, DL3, and/or CHX, and LNCaP cells (C) are treated for 24 hr as indicated. Cell lysates are prepared and analyzed by western blotting. The time course analysis reveals that the downregulation can be observed 8 hr after exposure of LNCaP cells to 20 µM DL3 and becomes much more significant at 24 and 48 hr (FIG. 9A). This effect of DL3 is also observed in LNCaP cells growing in SMEM (FIG. 9B, lane 2 vs. lane 1). DHT, which is known to prolong the half-life of AR, elevates AR and PSA expression in the cells. This effect of DHT is blocked by DL3 (FIG. 9B, lane 4 vs. lane 3). Expression of AR is diminished in cells exposed to the protein synthesis inhibitor cycloheximide (CHX), which is partially reversed by addition of DHT. This effect of DHT is also blocked by DL3 (FIG. 9B, lane 7 vs. lane 6), suggesting that the downregulation of AR by DL3 is at least partially due to the reduction of AR protein stability. To further determine how DL3 downregulates AR, LNCaP cells are incubated for 24 hr with DL3 in the absence or presence of proteasome inhibitor MG132. The data in FIG. 9C shows that DL3-induced reduction of AR is reversed by MG132, suggesting that DL3 promoted proteasome-mediated degradation of AR.

Effects of DL3 on Hsp70 Expression

As shown in FIG. 9, DL3 downregulates hsp70 expression. Hsp70 and hsp90 are key molecular chaperones in cells. Along with several co-chaperones, hsp70 and hsp90 play critical roles in folding and assembling AR to a high-affinity ligand binding conformation and in regulating AR activation that occurs following hormone binding. Therefore, the possibility of whether the downregulation of AR protein by DL3 is mediated by its effects on hsp70 or hsp90 expression is investigated. As shown in FIG. 9A, expression of hsp70, but not hsp90, is reduced in cells treated with DL3, which starts 4 hr after the treatment and remains downregulated during the experiment period (48 hr). The expression of hsp70 is also reduced in cells treated with DHT or CHX (FIG. 9B, lane 3 or 5 vs. lane 1).

Downregulation of hsp70 expression by DL3 is AR-dependent. Thus, the effects of DL3 on hsp70 expression are further investigated in several other prostate cancer cell lines, including LAPC-4 (wildtype AR), 22Rv1 (mutant AR), and AR-negative cell lines PC-3, DU-145, PWE1-NB14 (ATCC), and PWE1-NB26 (ATCC). Interestingly, the downregulation of hsp70 expression by DL3 is found in only the cells expressing AR (FIG. 10, panel A and panel B). In FIG. 10, LAPC-4 (in SMEM) and all other (in CMEM) cells are treated for 24 hr and analyzed by western blotting. LNCaP cells are transfected for 24 hr with hsp70 or its control vector, then treated for 24 hr. Thus, the above observation is further validated in PC-3 cells stably transfected with wildtype AR (PC-3AR). As shown in left panel C of FIG. 10, expression of hsp70 is moderately reduced in cells transfected with AR. Treatment with DL3 downregulates hsp70 expression in PC-3AR cells, but not PC-3 cells (FIG. 10, panel C, left). On the other hand, overexpression of hsp70 in LNCaP cells elevates endogenous AR protein levels (FIG. 10, panel C, right). However, overexpression of hsp70 is not able to protect AR downregulation by DL3 (FIG. 10, panel C, right). Thus, the downregulation of hsp70 in prostate cancer cells by DL3 is in an AR-dependent event.

Effects of DL3 on AR Nuclear Localization

Figure 11:
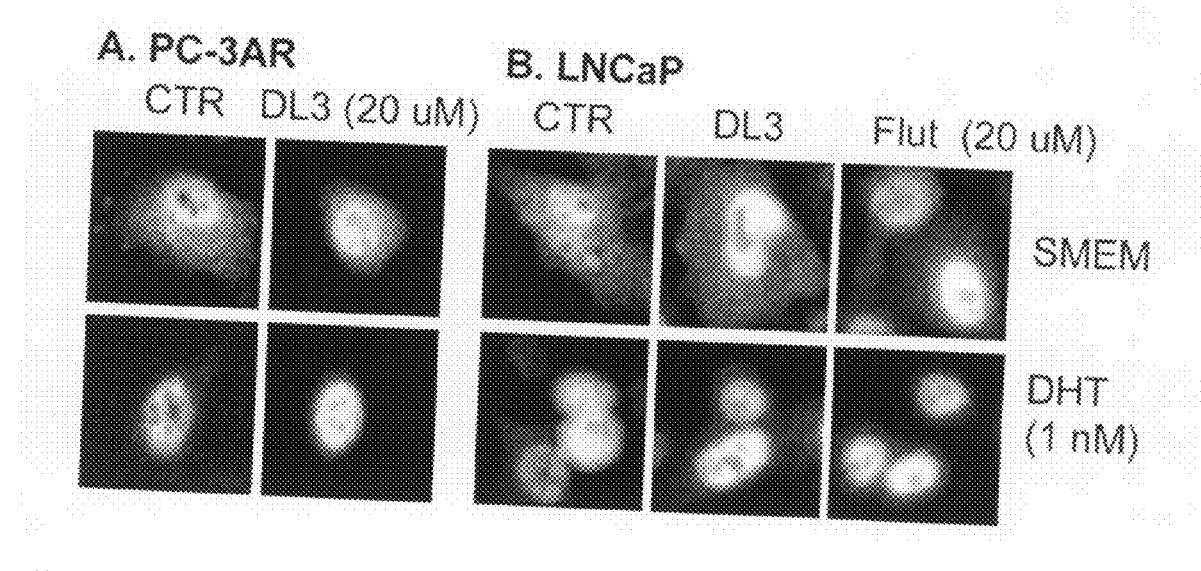
FIGS. 11A and 11B are sets of pictures showing the effects of DL3 on AR nuclear localization according to one embodiment.

AR nuclear translocation is a necessary step for AR action. To determine whether the inhibitory effects of DL3 on AR signaling are mediated by blocking AR nuclear translocation, the effects of DL3 on AR nuclear localization is investigated. In FIG. 11 cells in SMEM are treated for 30 min with 20 µM of DL3, followed by incubation for 2 h with 1 nM DHT in the presence or absence of 20 µM of DL3 or flutamide. AR in the cells were stained with an antibody to AR and detected with Texas Red-labeled secondary antibody. As shown in FIG. 11, AR is diffusely distributed in both the cytoplasm and nucleus in untreated PC-3AR and LNCaP cells. AR is translocated to the nuclei upon treatment with DHT. DL3, as well as flutamide, partially induce and enhance DHT-induced nuclear localization of AR. Thus, DL3 binds to AR.

Figure 12:
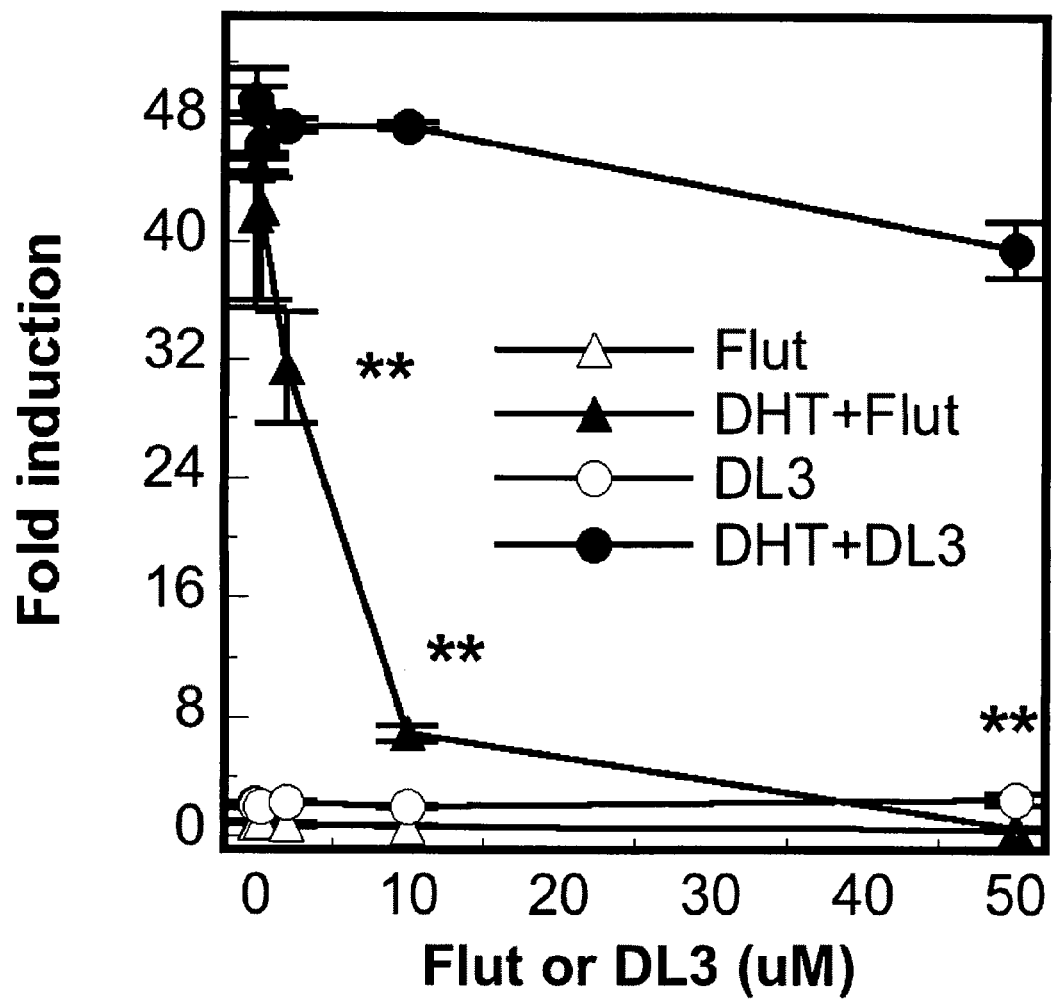
FIG. 12 is an illustration showing the effects of DL3 and Flut on AR N/C interaction according to one embodiment.

To further determine whether DL3 alters the interaction between DHT and AR, the effects of DL3 on the AR N/C interaction is investigated as seen in FIG. 12. This is done in a mammalian two-hybrid system, in which HeLa cells are cotransfected with vectors encoding the luciferase reporter driven by a tandem GAL4-responsive elements (GAL4-luc), the AR LBD and GAL4 DBD fusion protein (GAL4-LBD), and AR NTD and VP16 transactivation domain fusion protein (VP16-NTD). In FIG. 12, Hela cells are transiently contransfected for 24 hr with GAL4-luc GAL4-LBDF, and NTD-VP16 vectors, following treatment for 24 hr with 1 nM DHT and/or different concentrations of DL3 of Flut. Increase activity if measured. The data in FIG. 12 shows that the luciferase activity is not significantly altered by either DL3 or Flut and is increased by approximately 50 fold in cells treated with 1 nM of DHT. Flut inhibits DHT-stimulated N/C interaction in a dose-dependent manner. In contrast, the DHT-induced N/C interaction is not significantly altered by DL3 (FIG. 12).

The foregoing description of various embodiments and principles of the invention has been presented for the purposes of illustration and description. It is not intended to be exhaustive or to limit the inventions to the precise forms disclosed. Many alternatives, modifications, and variations will be apparent to those skilled the art. Moreover, although multiple inventive aspects and principles have been presented, these need not be utilized in combination, and various combinations of inventive aspects and principles are possible in light of the various embodiments provided above. Accordingly, the above description is intended to embrace all possible alternatives, modifications, aspects, combinations, principles, and variations that have been discussed or suggested herein, as well as all others that fall within the principles, spirit and scope of the inventions as defined by the claims.

What is claimed is:

1. A method for treating an individual having a disorder affected by androgen receptor activity, comprising administering a therapeutic amount of DL3 (6-amino-2-(2-4-tert-butyl-phenoxy)-ethylsulfanyl)-1H-pyrimidin-4-one) to the individual, wherein the disorder is selected from the group consisting of: prostate cancer, benign prostatic hyperplasia, hair loss, and combinations thereof.

2. The method of claim 1, wherein the disorder comprises prostate cancer.

3. The method of claim 1, wherein the therapeutic amount of DL3 is administered at a concentration from about 1 µM to about 50 µM.

4. The method of claim 3, wherein the therapeutic amount of DL3 is administered at a concentration from about 1 µM to about 10 µM.

5. The method of claim 3, wherein the therapeutic amount of DL3 is administered at a concentration from about 5 µM to about 40 µM.

6. A method for treating prostate cancer, comprising administering to an individual having prostate cancer a therapeutic amount of an androgen receptor antagonist, wherein the androgen receptor antagonist reduces the production of prostate specific antigen and has no negligible androgen receptor agonist effects, wherein the androgen receptor antagonist is DL3 (6-amino-2-(2-4-tert-butyl-phenoxy)-ethylsulfanyl)-1H-pyrimidin-4-one).

7. The method of claim 6, wherein the androgen receptor antagonist does not induce androgen withdrawal symptom.

8. The method of claim 7, wherein the therapeutic amount is administered in a concentration from about 1 µM to about 50 µM.

9. A method for treating prostate cancer, comprising administering to an individual having prostate cancer affected by androgen receptor activity a therapeutic amount of DL3 (6-amino-2-(2-4-tert-butyl-phenoxy)-ethylsulfanyl)-1H-pyrimidin-4-one).

10. The method of claim 9, wherein the act of administering comprises oral administration.

11. The method of claim 9, further comprising administering an additional cancer treatment to the individual.

12. The method of claim 11, wherein the additional cancer treatment comprises chemotherapy.

13. The method of claim 11, wherein the additional cancer treatment comprises a nonsteroidal antiandrogen.

14. The method of claim 13, wherein the nonsteroidal antiandrogen is selected from the group consisting of flutamide, nilutamide, and bicalutamide.

15. The method of claim 14, wherein the therapeutic amount of DL3 is administered at a concentration from about 1 µM to about 50 µM.

16. The method of claim 13, wherein the therapeutic amount of DL3 is administered at a concentration from about 5 µM to about 20 µM.

* * * * *